United States Patent [19]

Bartel

[11] Patent Number: 5,759,032
[45] Date of Patent: Jun. 2, 1998

[54] DEVICE FOR APPLYING PRESSURE TO PHOTOCURABLE MATERIALS DURING POLYMERIZATION

[76] Inventor: William B. Bartel, 7890 E. Cactus Wren Rd., Scottsdale, Ariz. 85250

[21] Appl. No.: 685,481

[22] Filed: Jul. 24, 1996

[51] Int. Cl.$^6$ .............................. A61C 1/00; A61C 3/00
[52] U.S. Cl. .................. 433/29; 385/43; 385/902
[58] Field of Search .................... 433/29, 141, 215, 433/229, 25; 385/43, 902

[56] References Cited

U.S. PATENT DOCUMENTS

| | | | |
|---|---|---|---|
| 2,240,402 | 4/1941 | Joroslow | 385/902 X |
| 2,932,294 | 4/1960 | Fourestier | 433/29 X |
| 4,503,853 | 3/1985 | Ota et al. | 385/902 X |
| 4,522,594 | 6/1985 | Stark et al. | 433/141 |
| 4,571,188 | 2/1986 | Hamilton | 433/226 |
| 4,666,406 | 5/1987 | Kanca, III | 385/902 X |
| 4,682,950 | 7/1987 | Dragan | 433/90 |
| 4,723,825 | 2/1988 | Herold | 433/141 |
| 5,104,591 | 4/1992 | Masuhara et al. | 264/16 |
| 5,119,461 | 6/1992 | Beyer et al. | 385/902 X |
| 5,259,761 | 11/1993 | Schnettler et al. | 433/29 X |
| 5,290,169 | 3/1994 | Friedman et al. | 433/29 |
| 5,415,543 | 5/1995 | Rozmajzl, Jr. | 433/29 |

*Primary Examiner*—Nicholas D. Lucchesi
*Attorney, Agent, or Firm*—Paula L. Bentley

[57] ABSTRACT

A dental curing accessory that fits on the light emitting tip of a curing light and is pressed against a photocurable material and its immediate underlying structure such as a tooth, appliance, or dental structure while the photocurable material is polymerizing. The present invention is a partially hollow tubular body having a receiving portion which fits onto the curing light tip, and also has a light permitting contact portion which contacts the photocurable material transferring pressure from the device to the photocuring site. Pressure delivered to the photocuring site through the present invention promotes intimate contact between a photocurable material and a structure to which the photocurable material is bonded or attached to, providing a stronger bond, reducing voids in the photocurable material, contouring the photocurable material against the structure resulting in a more even surfaced product requiring less finishing work, and substantially preventing the formation of an oxygen inhibited layer. The present invention may also include a reflective material positioned on or positioned within the tubular body wall for reducing the amount of light escaping from the tubular body, or alternatively, the tubular body may be made of a reflective material which does not permit an appreciable amount of light to escape the device.

20 Claims, 2 Drawing Sheets

DEVICE FOR APPLYING PRESSURE TO PHOTOCURABLE MATERIALS DURING POLYMERIZATION

BACKGROUND OF THE INVENTION

The present invention relates generally to a dental photocuring accessory and specifically to a device that fits on the light emitting end of a dental curing light. Photocurable dental materials are materials widely used in the dental art that are polymerized (cured) when radiated by light and used for a wide variety of purposes including restoring a tooth structure or dental prosthesis, and bonding or adhering dental articles to a tooth structure/prosthesis. The curing of photocurable dental materials placed on tooth structure in a patient's mouth is commonly accomplished simply by placing the light emitting tip of a portable or hand held curing light directly over the material to be cured, then activating the light source until the photocurable material has sufficiently polymerized.

Several problems are associated with current intraoral photocuring practices due to the hard tip of the curing light not being able to conform to tooth structure, dental fibers and other dental materials being bonded or adhered to tooth structures. In particular, when bonding dental fiber or ribbon to an abutment tooth in preparation for constructing a fixed bridge, it is difficult to bring the fiber into intimate contact with the underlying abutment tooth structure because the fiber tends to flex away from the tooth. A "dental fiber" is a string like strip used to bind or tie structures together. In addition, frays at the end of dental fiber tend to protrude away from the abutment tooth making finishing more difficult as well as weakening the bond holding the fiber to tooth structure and/or restorative laid over the fiber. The current practice is to use instruments to hold down the ends of the fiber during curing, but this method is unsatisfactory because the instruments block the polymerizing light being radiated on the photocurable bonding resins and at best only bring a portion of the fiber into intimate contact with tooth structure, thus producing a less than optimal bond that is more likely to break.

Another problem with photocurable materials is the tendency of voids, bubbles or spaces to be incorporated into photocurable materials prior to curing which if not removed results in a porous cured material which is easily stained, more likely to absorb water and break, and/or makes for a weaker bond. U.S. Pat. No. 4,682,950 (Dragan) has attempted to address the problem with voids by providing a dispensing device that extrudes a thin sheet of photocurable composite onto a tooth structure thereby reducing the extent that a photocurable materials must be manipulated when applied as a veneer prior to curing. But this device is only suitable for veneering and therefore not widely applicable. A solution for minimizing voids is still needed for other restorative applications.

A third problem with photocurable materials is the tendency for photocurable resins, typically having lower viscosity than other dental photocurable materials, to deform or shrink during curing due to the contraction of the resin. U.S. Pat. No. 5,104,591 (Masuhara et al.) attempts to address this problem by teaching an extraoral procedure involving covering a photocurable resin on a dental prosthesis with a film in a confined container then applying pressurized gas to the film simultaneously during light curing to reduce shrinkage. However, this pressurized gas apparatus obviously cannot be used for any intraoral curing of photocurable resins. A method for applying pressure during curing outside a confined container in extraoral and intraoral situations is still needed.

The polymerization of most if not all photocurable materials is inhibited in the presence of oxygen producing an uncured layer of material on any oxygen exposed surface of photocured materials. An oxygen inhibited layer is undesirable for many dental applications for at least two reasons, first, it results in a weaker bond and second, it often results in a cured product with an uneven surface. To prevent the formation of an oxygen inhibited layer, an oxygen free environment must be provided. Providing an oxygen free curing environment in extraoral applications has been accomplished by photocuring in an oxygen free container like that taught in Masuhara et al., supra. The oxygen free container method of photocuring is completely unsuitable for intraoral curing for obvious reasons. U. S. Pat. No. 5,415,543 (Rozmajzl, Jr.) attempts to provide an oxygen free environment for intraoral photocuring by delivering a blanket of inert gas to an intraoral curing site thus displacing ambient oxygen and reducing the oxygen inhibited layer. However, the Rozmajzl, Jr. approach not only adds another step and piece of equipment, but also poses risks and involves precautions that make it undesirable for intraoral use. A simpler, safer method is still needed.

A final problem with photocurable materials is that the surface of hardened photocured material is often uneven or in a poorly contoured shape that requires substantial finishing work due to uneven curing (due to an oxygen inhibited layer for example) and/or uneven application of the photocurable material. The most desirable cured product is one that is as even and smooth as possible thus reducing the amount of burring and polishing required to obtain a smooth finish. The dental art has not fully responded to the problem of uneven photocured surfaces. Dragan, as discussed above, teaches a very limited solution in the form of a dispenser for laying down photocurable restorative veneers. U.S. Pat. No. 4,571,188 (Hamilton) also teaches another very limited solution that restores original occlusal anatomy to a filled tooth by pressing a transparent occlusal impression onto a prepared tooth cavity filled with a photocurable composite at the same time the photocurable composite is being irradiated with a curing light. However, neither of these approaches provides a solution that can be applied to other dental restorations and applications.

A need therefore still exists in the art for a simple and widely applicable way to increase the degree of intimate contact between photocurable materials and the structure(s) they bond or adhere to, reduce voids in photocurable materials prior to curing, prevent contraction during curing, prevent the formation of an oxygen inhibited layer, and provide a more even surfaced product after curing. It is to this end that the present invention is addressed.

BRIEF SUMMARY OF THE INVENTION

The present invention relates to the field of dentistry, and more especially to the field of restorative dentistry employing photocurable composites and resins. The present invention involves a partially hollow, tubular device which fits onto the light emitting end of a curing light and is pressed directly or indirectly against a photocurable dental material during the time the photocurable material is exposed to light from the curing light. A curing light includes any electromagnetic emitter used to cure photocurable materials, including but not limited to visible light and laser emitters.

The pressing or contact portion of the present invention terminates in a supple outer end which when pressure is applied, presses a photocurable material into intimate contact with the underlying structure to which the photocurable material is to adhere or bond to during the curing phase. As a result of applying direct pressure during the curing exposure, intimate contact between the photocurable material and underlying structure is achieved, voids and bubbles in the surface of the photocurable material are pressed out, the photocurable material is held down and contraction minimized, atmospheric air is displaced by the outer end providing an oxygen free environment during photocuring, and the photocured product is more likely to be even surfaced and/or closely contoured to the underlying tooth structure. The general result is a stronger bond and a cured product that is easier to finish. And, in the specific examples of bonding a dental fiber to abutment teeth for making a fixed bridge to replace a missing tooth, or, splinting teeth together with fiber and resins, the present invention presses the entire fiber into close approximation of the abutment tooth resulting in a fiber-abutment tooth bond that is much less likely to detach.

Generally, the present invention can be made of any material or combination of materials which permits a photocurably effective amount of light to pass from the curing light tip and out through the supple outer end. That is, the filled or axial region of the contact portion of the tubular body must be made of a light permitting material to allow a photocurably sufficient amount of light to pass from the curing light through the supple outer end to the curing site.

Where the material or combination of materials of which the present invention is made of allows light to escape from the tubular body, the present invention may also include means for preventing a significant amount of curing light emissions from escaping said device. Said means may involve making all or part of the tubular body wall out of a reflective material so as to prevent a substantial amount of light from escaping the present invention. For example, making the tubular body wall of a white or light-colored plastic would be one effective way of reflecting curing light back into the interior of the present invention so that it is available for curing. Alternatively, said means may be a reflective material positioned on the outer tubular body wall, on the inner tubular body wall, or even within the tubular body wall. Henceforth, the term "positioned on" shall mean positioned on or positioned within. "Reflective material" means any material that can be positioned on the tubular body of the present invention in a way to reduce emitted light escapement, or alternatively, any material of which said tubular body can be made of to achieve the same purpose, and includes opaque, metallic and any other light reflecting substances that may be coated on, wrapped around, or contained within the tubular body of the present invention. Some examples of the form said reflective material can take include: a band, coating, covering, paint, film, layer, electroplate, membrane, fibers and a plurality of flecks. It should be evident to the skilled artisan that the present invention may be fashioned in a multitude of ways that would insure a sufficient amount of light emitted from the curing light arrives at the photocuring site. These alternatives are included within the scope of this invention.

The outer end of the present invention must be supple or yielding to enable the present invention to be effective in pressing and/or shaping photocurable materials against a broad range of underlying tooth structures. Thus, the shape of the supple outer end can be shaped in any way so to further distribute the applied pressure in a more advantageous manner, and/or, to better shape the photocurable material. Possible outer end shapes include concave, convex, flat and wedge-like. The outer end may protrude outward. For example: a convex shaped outer end is especially useful for applications where deep preparations are filled with photocurable composites; a flat or concave shaped outer end is usually better for pressing photocurable composites into shallow preparations and facial surfaces, or, for placing dental fiber onto an etched surface with little or no preparation; a concave shaped outer end is usually better for shaping a photocurable composite against a facial tooth surface; and, a wedge-like shaped outer end is especially useful for curing photocurable materials on proximal and cervical surfaces. The overall outer end shape need not be A-symmetrical, for example, an outer end with a concave outer end may be elliptically concave as well as spherically concave, or even irregularly concave. Just what outer end shape is best depends on the particular application.

It should be evident that while the present invention is particularly useful for intraoral applications, the present invention may be used extraorally as well. Intraoral photocuring means curing photocurable materials inside a patient's mouth. Extraoral photocuring means curing photocurable materials outside the mouth, for example, repairing dentures, bridges and other laboratory procedures. It should also be evident that the present invention can be used in a variety of extraoral or intraoral applications.

Accordingly, it is a prime objective of the present invention to provide an improved and novel device which allows pressure to be applied against a photocurable material simultaneously while said photocurable material is being cured.

A further object of the present invention is to provide a novel device for pressing photocurable materials into intimate contact with an underlying structure to improve bond strength.

Another object of the present invention is to provide a new and useful device which can reduce voids in photocurable materials.

Yet another object of the present invention is to provide a unique device for minimizing contraction of photocurable resins during curing.

A further object of the present invention is to provide a device which shapes photocurable composites and restoratives into a more even surfaced and/or tooth contoured product requiring less finishing.

Still another object of the present invention is to provide a dental photocuring accessory that adds pressure during intraoral photocuring. Yet another object of the present invention is to provide a new and useful device for removing oxygen from the immediate environment of photocurable materials during curing thereby preventing the formation of an oxygen inhibited layer.

Another object of the present invention is to provide a new and useful device for pressing indirect laminates or restorations in place while curing.

These and still further objects as shall hereinafter appear are fulfilled by the present invention in a remarkably unexpected manner as will be readily discerned from the following detailed description of exemplary embodiments thereof.

DESCRIPTION OF THE PREFERRED EMBODIMENT

Generally, the present invention is a partially hollow, tubular body having an upper hollow receiving portion for receiving the tip of a curing light and a lower filled or solid contact portion for pressing onto a photocurable material and its immediate underlying dental structure. The axial region of the lower contact portion is occupied with a light permitting material that will allow a photocurably sufficient amount of light to pass from the curing light to the curing site. The tubular body can be of any shape that allows the present invention to fit on the tip of the curing light and provide sufficient contact area to adequately cover as much photocurable material and its underlying tooth/dental structure as needed for a particular application. The overall shape of the tubular body can include: cylindrical as shown in FIGS. 1-8, block shaped like that in FIG. 9, or a nonstandard shape such as that shown in FIGS. 10 and 11.

The topography of the outer end that comes into contact with a photocurable material can be any shape that distributes the applied manual pressure in the most advantageous manner for a given application. The topography of the outer end can also be a shape that tends to sculpt the photocurable material into a desired finished shape. In reaching these aims, the outer end of the present invention may possess varying degrees of convexity or concavity, may be flat, slanted, or wedged in varying angles of acuity (see FIGS. 10 and 11), or, can spherically or elliptically swell out from the tubular body. It may even be possible to make the outer end of the contact portion a detachable and interchangeable part of the contact portion of the present invention. In sum, the exact shape of the tubular body, the receiving end, and the outer end of the present invention are all driven by the particular application for which it will be used.

Figure 1:
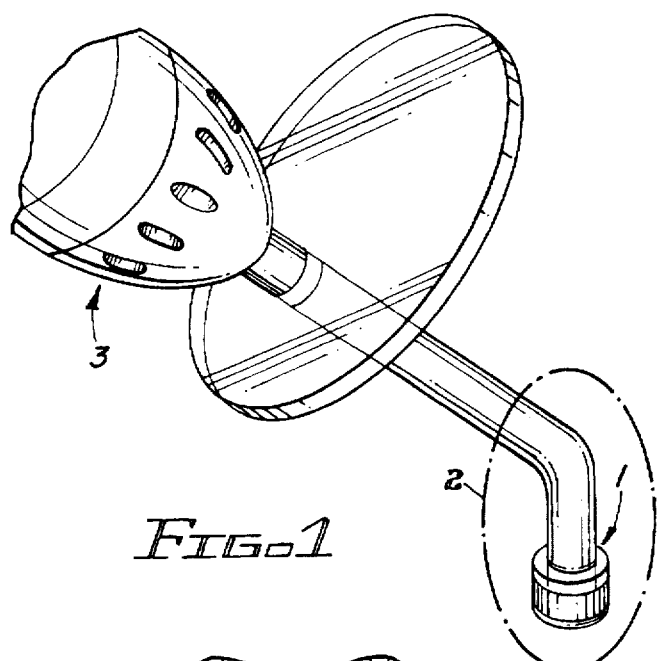
FIG. 1 is a perspective view of a first embodiment of the present invention having a flat outer end and connected to the tip of a curing light in readiness for use.
Figure 2:
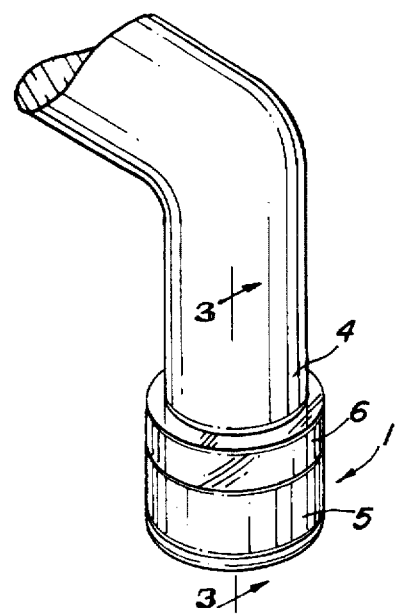
FIG. 2 is an enlarged view of said first embodiment and curing light tip of FIG. 1.
Figure 3:
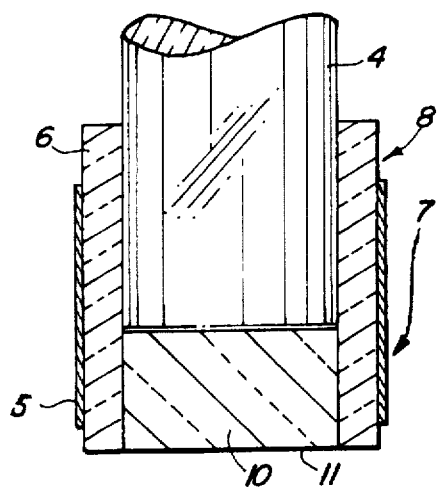
FIG. 3 is a cross sectional view of said first embodiment of the present invention along line 3 of FIG. 2.
Figure 4:
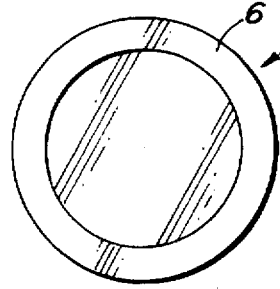
FIG. 4 is a top plan view of the first embodiment depicted in FIG. 1.
Figure 5:
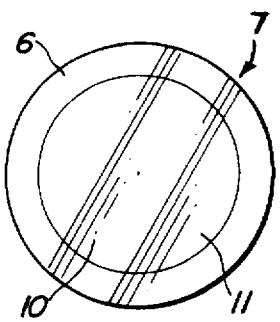
FIG. 5 is a bottom plan view of the first embodiment depicted in FIG. 1.

Referring now to FIGS. 1, 2, 3, 4 and 5, a preferred embodiment of the present invention is disclosed as a cylindrically shaped device (1) comprising a 14 mm long segment of clear plastic flexible tubing (6) (7 mm in diameter) partially filled with a clear supple filler material such as methylstyrene polymer (CAS 9011-11-4) (10), thereby forming a hollow receiving portion (8) and a filled/ occupied contact portion (7). Tubing (6) has an aluminum band (5) affixed around its outer wall so that said band (5) is positioned as shown in FIG. 3 providing means for preventing a significant amount of light emitting from curing light (3) from escaping device (1). Receiving portion (8) closely approximates the shape of a curing light tip (4) and allows tip (4) to be received by receiving portion (8) and touch contact portion (7). A flat outer end (11) of contact portion (7), was formed by placing said plastic tubing on a flat surface during the filling of contact portion (7), above. When in use, the flat contact portion will come into direct or indirect contact with a photocurable material and its underlying tooth/dental structure.

Figure 6:
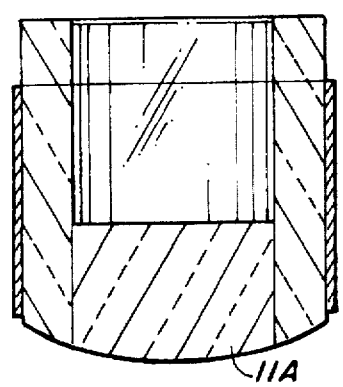
FIG. 6 is a cross sectional view of a second embodiment of the present invention similar to said first embodiment except having a convex outer end.

Referring now to FIG. 6, a second preferred embodiment of the present invention is shown, said second embodiment made in a similar manner and of similar materials as the embodiment of FIG. 3 except a convex outer end (11A) was formed by building up additional polymer from the bottom end of said contact portion before the polymer was set until the disclosed shape was attained.

Figure 7:
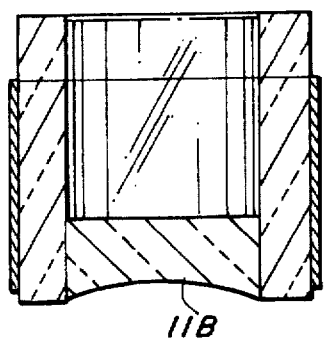
FIG. 7 is a cross sectional view of a third embodiment of the present invention similar to said first embodiment except having a concave outer end.

Referring now to FIG. 7, a third preferred embodiment of the present invention is shown, said third embodiment made in a similar manner and of similar materials as the embodiment of FIG. 3 except a concave outer end (11B) was formed by scooping out some of the polymer from the bottom end of said contact portion before the polymer was set until the disclosed shape was attained.

Figure 8:
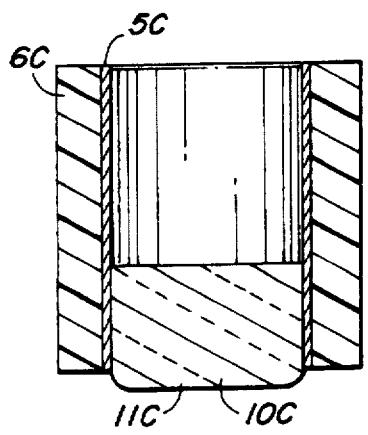
FIG. 8 is a cross sectional view of a forth embodiment of the present invention similar to said first embodiment except having a flat, protruding outer end.

Referring now to FIG. 8, a forth embodiment of the present invention is shown, said forth embodiment made in a similar manner and of similar materials as the embodiment of FIG. 3 except a reflective coating (5C) is applied to the inside wall of a plastic tube (6C) prior to filling tube (6C) with said clear supple material (10C) to provide a means for preventing a significant amount of light emitting from a curing light from escaping the device of FIG. 8. The outer end (1C) is flat and made to protrude just beyond the end of the wall (6C) of said tubing by building up filling material (10C) thereby allowing additional room for compression.

Figure 9:
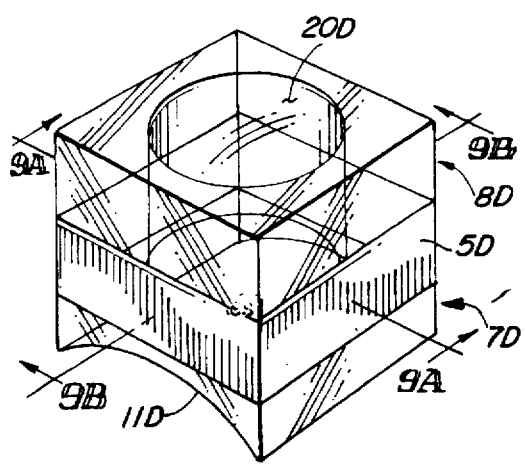
FIG. 9 is a perspective view of a fifth embodiment of the present invention showing a block shaped device with a concave outer end.
Figure 9A:
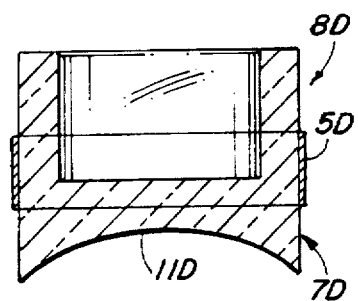
FIG. 9A is a cross sectional view of said fifth embodiment along line 9A in FIG. 9.
Figure 9B:
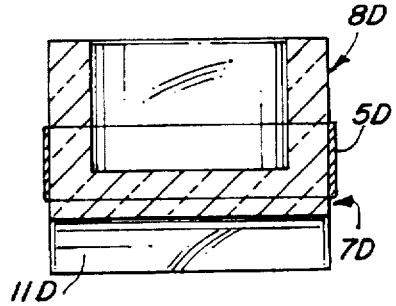
FIG. 9B is a cross sectional view of said fifth embodiment along line 9B in FIG. 9.

Referring now to FIGS. 9, 9A, and 9B, a fifth embodiment of the present invention is shown, said fifth embodiment being block shaped and having a receiving portion (8D) with a cylindrical cavity (20D) for receiving the tip of a curing light (not shown), a contact portion (7D) with a concave outer end (11D), and a metallic band (5D) wrapped and secured around contact portion (7D). The integral device of FIG. 9 is molded according to ordinary practices and made of any clear, supple plastic.

Figure 10:
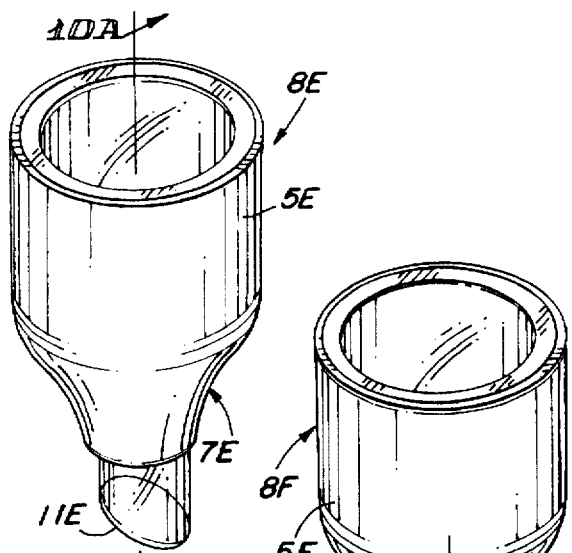
FIG. 10 is a perspective view of a sixth embodiment of the present invention having a protruding wedge shaped outer end.
Figure 10A:
FIG. 10A is a cross sectional view of said sixth embodiment along line 10A in FIG. 10.

Referring now to FIGS. 10 and 10A, a sixth embodiment of the present invention is shown, said sixth embodiment being made of a clear, supple plastic that is molded into an integral cup like receiving portion (8E) and a contact portion (7E) having a slightly concave wedge like outer end (11E). A white, reflective paint (5E) is applied to the outside of said device as shown to provide means for maximizing the amount of emitted light delivered to the curing site.

Figure 11:
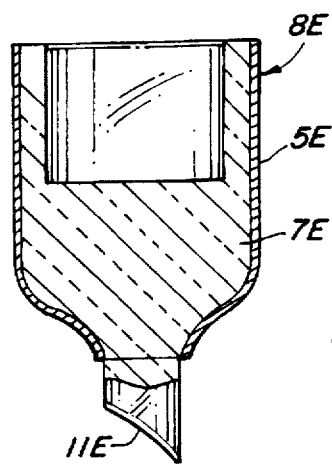
FIG. 11 is a perspective view of a seventh embodiment of the present invention having a wedged, tongue like outer end.
Figure 11A:
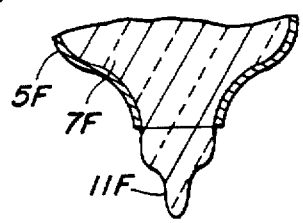
FIG. 11A is a cross sectional view of said seventh embodiment along line 11 A in FIG. 11.

Referring now to FIGS. 11 and 11A, a seventh embodiment of the present invention is shown, said seventh embodiment being made of a clear, supple plastic that is molded into an integral cup like receiving portion (8F) and a contact portion (7F) having a tongue like wedge shaped outer end (11F). The outside surface of said embodiment is covered with a white paint (5F) to provide means for maximizing the amount of emitted light delivered to the curing site.

To further aid in the understanding of the present invention and not by way of limitation, the following examples of how to use the present invention are presented.

EXAMPLE 1

Teeth may be splinted together with dental fiber to prevent tooth movement after orthodontic therapy, in compromised periodontal situations or cases where there are unstable occlusal problems. There is little or no preparation other than etching the tooth structure to which a dental fiber will be attached. The etched surface is first bonded with an unfilled resin. Dental fibers wetted with a similar unfilled resin are then laid on the etched tooth surfaces then light cured under pressure using the present invention joined to a curing light. Where the wetted fiber is bonded to a convex tooth surface, a concave ended device like that depicted in FIG. 7 is favored. Hand pressure on the curing light causes the present invention to press each fiber into intimate contact with the tooth thereby maximizing total bonded surface area and minimizing voids. The result is a stronger bond between tooth and fibers that is much less likely to break.

Next, a first layer of photocurable composite is applied over the bonded fiber-tooth surface and pressed into place with the concave end of the present invention, but said first layer is cured with a curing light alone. It is desirable when building up multiple layers of composite to have an oxygen inhibited layer of photocurable material on the surface of the previously cured layer because the uncured surface enables that layer and the next layer to better adhere to one another. The second and, for this example, final layer of photocurable composite is placed into a previously formed clear matrix having the desired finished tooth form. The composite loaded matrix is then placed over the first layer above (cured composite with the oxygen inhibited layer) and press-photocured with a curing light having an embodiment of the present invention having a concave outer end attached thereto. As the curing light-present invention combination presses against the outside of the matrix, the composite in the matrix presses into intimate contact with the first composite layer and underlying tooth structure. The matrix is flexible and the present invention enables the operator to press the matrix closer to the finish lines of the tooth while curing thereby reducing the amount of trimming needed to finish the tooth.

Generally, it may be advantageous whenever pressing the claimed invention against a photocurable material and underlying structure for the operator to place the thumb on the bend of the curing light and a finger of the same hand behind the tooth structure being bonded or restored and bringing the thumb and finger closer together in a pinching like motion to produce the desired pressure placing effect. Alternately, simple hand or finger pressure may be applied against the bend of the curing light. Other methods of transferring pressure from the hand to the curing site may be utilized, the best method depends on the given procedure, the location of the working site and personal preference of the operator.

If splinting involves bonding a resin or composite to a facial or lingual tooth surface, it may be preferred to use a device of the present invention having a flat surfaced contact portion like that depicted in FIGS. 3 or 8.

EXAMPLE 2

This example involves the making of a fixed bridge with dental fibers, resin and composite. Concave preparations are cut into the facial, lingual and proximal surfaces of the abutment teeth and then etched and bonded by unfilled photocurable resin in a manner similar to that in Example 1. Fibers wet with like resins are then bonded to the prepared abutment tooth surfaces using the present invention in a similar manner described in Example 1. Where the preparation is concave, the preferred contact portion outer end is convex like that depicted in FIG. 6 because it forces the fibers against the prepared surface of the tooth thereby maximizing the surface area between the underlying tooth preparation and fibers. The remaining procedures of restoring the bridge is similar to splinting teeth above. Multiple layers of photocurable composite are individually pressure cured over the bonded fibers with the aid of the present invention until the bridge is completed.

EXAMPLE 3

Class I restorations restore the occlusal surfaces of the teeth. This is usually a small restoration on the biting surface of a molar or bicuspid. The surface is etched and bonded with an unfilled resin in the usual manner. Photocurable composite resin is placed against the bonded unfilled resin. The occlusal restoration is usually built up with composite layers (previous layers are cured before next layer is laid down) if the preparation is more than 1.5 mm deep in a manner similar to that in Example 1. The final contour of the occlusal surface is shaped with a thin dental instrument before curing. The final layer of composite is cured with a curing light attached to the present invention having a convex outer end like that depicted in FIG. 6. If the composite was well contoured before the outer end was applied, the final surface usually requires very little finishing and polishing. If the occlusal surface of a mandibular tooth is being restored, pressure can best be applied by placing the index finger on the bend of the curing light wand and the thumb under the border of the mandible and squeezing. These restorations usually have no oxygen inhibited layer on the final composite layer if the entire occlusal surface is covered by the outer end.

EXAMPLE 4

Class II restorations are similar to Class I restorations but also involve a proximal surface of the tooth. After cavity preparation, etching and unfilled resin bonding is completed, a matrix band is placed around the tooth to be restored thereby forming the contour for the proximal surface. Usually a wedge is placed at the gum line between the proximal surface and the adjacent tooth. The wedge pushes the matrix band against the tooth being restored to keep from getting an overhang of cured composite material. The composite restoration is layered in 0.5 to 1.0 mm layers in a manner similar as that described above until the final layer is placed. The final layer is pressure cured using the claimed invention having a wedge shape as shown in FIG. 10, then finished according to standard dental practices.

EXAMPLE 5

Class V restorations are restorations located at the gum line or cervical area of the teeth. After cavity preparation is made and the tooth is etched and bonded with unfilled resin, a photocurable composite is placed into the preparation and contoured with instruments to blend with normal tooth contours. The photocurable composite is then cured with the curing light while pressing an embodiment of the present invention having an outer end with a concave outer portion against the restoration. The cured composite is then finished and polished.

EXAMPLE 6

This example involves the replacement of a tooth surface with a ceramic and resin laminate. After etching the tooth surface and bonding with an unfilled resin as described in the examples above, a ceramic laminate is seated on the prepared tooth surface with photocurable luting resin between the laminate and the tooth. The ceramic laminate is pressed against the tooth with the present invention while simultaneously exposing underlying luting resin to light from the curing light for a short period of about 5 seconds (light passes through the ceramic laminate to the luting resin below). Excess luting resin is then cleaned off the present invention and the present invention is again placed against the laminate and the underlying luting resin cured for about 60 seconds or until sufficiently polymerized. If the ceramic restoration is convex, the pressing device should have a concave outer end like that depicted in FIG. 7. If the ceramic restoration is flat, the present invention should be flat as depicted in FIG. 3 or 8.

EXAMPLE 6

This example involves the placement of ceramic and resin inlays and onlays. The tooth receiving the inlay/onlay is etched and prepared according to standard dental procedures. The inlay/onlay is placed on the prepared tooth with photocurable luting resin between the tooth and the inlay/onlay. The inlay/onlay is then pressed upon with the present invention to hold it in place while simultaneously curing the underlying luting resin until sufficiently polymerized. The present invention should be large enough to extend beyond the inlay/onlay and onto the surrounding tooth structure. This prevents an oxygen inhibited layer from forming on the surface of the luting resin occupying the gap between the inlay/onlay and the tooth that would cause an undesirable, microscopic, shallow gap termed a marginal deficiency to form between the inlay/onlay and the tooth. The shape of the outer end should be concave if the inlay/onlay is on a convex surface, and flat if on a flat surface.

From the foregoing, it is readily apparent that useful embodiments of the present invention have been herein described and illustrated which fulfills all of the aforestated objectives in a remarkably unexpected fashion. It is of course understood that such modifications, alterations and adaptations as may readily occur to the skilled artisan confronted with this disclosure are intended within the spirit of this disclosure.

What is claimed is:

1. A device comprising:
    a partially hollow tubular body having a hollow upper receiving portion joined to a lower contact portion, said lower contact portion having an outer end and an axial region;
    wherein said receiving portion fits on the light emitting end of a curing light, wherein said axial region is occupied with a light permitting material that allows a photocurably effective amount of light to pass through, and wherein said outer end is supple.

2. The device according to claim 1, wherein at least a part of said tubular body is made of a reflective material.

3. The device according to claim 2, wherein said reflective material is an opaque plastic.

4. The device according to claim 1, wherein said device further includes means for preventing a significant amount of curing light emissions from escaping said device.

5. The device according to claim 4, wherein said means is a reflective material positioned on at least said contact portion less said outer end.

6. The device according to claim 5, wherein said reflective material is selected from the group consisting of an opaque substance, a metallic substance, and a light reflecting substance.

7. The device according to claim 5, wherein said reflective material is a reflective band.

8. The device according to claim 5, wherein said reflective material is a reflective coating.

9. The device according to claim 1, wherein the shape of said outer end is selected from the group consisting of flat, convex, concave, and wedge-like.

10. The device according to claim 9, wherein said device further includes means for preventing a significant amount of curing light emissions from escaping said device.

11. The device according to claim 10, wherein said means is a reflective material positioned on at least said contact portion less said outer end.

12. The device according to claim 11, wherein said reflective material is selected from the group consisting of an opaque substance, a metallic substance, and a light reflecting substance.

13. The device according to claim 11, wherein said reflective material is a reflective band.

14. The device according to claim 11, wherein said reflective material is a reflective coating.

15. The device according to claim 9, wherein at least a part of said tubular body is made of a reflective material.

16. The device according to claim 15, wherein said reflective material is an opaque plastic.

17. A device comprising:
    a tube; and
    a light permitting filler, said filler occupying the lower portion of said tube thereby comprising an axial region of said device, wherein said axial region has a supple outer end, and wherein the shape of said outer end is substantially shaped like that selected from the group consisting of a convex shape, a concave shape, a flat shape, and a wedge-like shape.

18. The device of claim 17, further including a reflective material positioned on said tube so as to substantially cover said axial region.

19. A device comprising an integral unit made of a supple, light permitting substance formed into a tubular body having a hollow receiving portion which fits on the tip of a curing light, and a contact portion having an outer end for pressing against a photocurable material, and wherein the shape of said outer end is substantially shaped like that selected from the group consisting of a convex shape, a concave shape, a flat shape, and a wedge-like shape.

20. The device of claim 20, further including a reflective material positioned around said contact portion so as to make a photocurably effective amount of light available for photocuring.

* * * * *